(12) United States Patent
Chugg et al.

(10) Patent No.: US 9,063,534 B2
(45) Date of Patent: Jun. 23, 2015

(54) WORKPIECE POSITIONING METHOD AND APPARATUS

(75) Inventors: Andrew Michael Chugg, Bristol (GB); Jonathan James Ward, Bristol (GB); James Robert McIntosh, Carterton (GB)

(73) Assignee: MBDA UK LIMITED, Hertfordshire (GB)

(*) Notice: Subject to any disclaimer, the term of this patent is extended or adjusted under 35 U.S.C. 154(b) by 24 days.

(21) Appl. No.: 13/321,712

(22) PCT Filed: Oct. 6, 2011

(86) PCT No.: PCT/EP2011/067509
§ 371 (c)(1),
(2), (4) Date: Mar. 12, 2012

(87) PCT Pub. No.: WO2012/049074
PCT Pub. Date: Apr. 19, 2012

(65) Prior Publication Data
US 2013/0190922 A1    Jul. 25, 2013

(30) Foreign Application Priority Data

Oct. 13, 2010 (GB) .................................. 1017412.6
Mar. 23, 2011 (EP) .................................. 11275045

(51) Int. Cl.
*G06F 19/00* (2011.01)
*G05B 19/19* (2006.01)
(Continued)

(52) U.S. Cl.
CPC ............... *G05B 19/19* (2013.01); *B23K 26/383* (2013.01); *G01N 21/9501* (2013.01);
(Continued)

(58) Field of Classification Search
CPC ............ B23K 26/383; B23K 26/0608; B23K 26/4065; B23K 26/0676; G05B 2219/34146; G01N 2201/0145; G01N 21/9501
USPC .......................................... 700/186, 187, 192
See application file for complete search history.

(56) References Cited

U.S. PATENT DOCUMENTS

| 4,128,968 | A | 12/1978 | Jones |
| 4,508,450 | A | 4/1985 | Ohshima et al. |

(Continued)

FOREIGN PATENT DOCUMENTS

| EP | 0 260 522 | 3/1988 |
| EP | 1 868 054 A1 | 12/2007 |

(Continued)

OTHER PUBLICATIONS

International Preliminary Report on Patentability together with Written Opinion of the International Searching Authority from related PCT/EP2011/067509, dated Apr. 25, 2013.

(Continued)

*Primary Examiner* — Michael D Masinick
(74) *Attorney, Agent, or Firm* — Scully, Scott, Murphy & Presser, P.C.

(57) ABSTRACT

A method of relatively positioning a workpiece and a reference axis comprising effecting relative displacements of the workpiece and the reference axis along orthogonal axes so that an intersection of the reference axis with the workpiece is moved at substantially constant speed along a curvilinear path.

The method is particularly applicable to SEE sensitivity mapping of a microchip memory using a pulsed laser, relative to the axis of which the chip is moved in a spiral path.

17 Claims, 3 Drawing Sheets

(51) Int. Cl.
  *G05B 19/41* (2006.01)
  *G05B 19/418* (2006.01)
  *B23K 26/38* (2014.01)
  *G01N 21/95* (2006.01)

(52) U.S. Cl.
  CPC ......... *G05B 19/41* (2013.01); *G05B 19/41875* (2013.01); *G05B 2219/34146* (2013.01); *G05B 2219/37224* (2013.01)

(56) References Cited

U.S. PATENT DOCUMENTS

| | | | |
|---|---|---|---|
| 4,704,688 A | 11/1987 | Kamata | |
| 4,995,102 A | 2/1991 | Ichinose et al. | |
| 5,034,877 A * | 7/1991 | Shultz | 700/61 |
| 5,043,589 A | 8/1991 | Smedt et al. | |
| 5,983,167 A | 11/1999 | Ebisawa | |
| 6,535,781 B1 | 3/2003 | Tsutsumi | |
| 8,122,317 B1 * | 2/2012 | Clark et al. | 714/758 |
| 2004/0081048 A1 | 4/2004 | Ulf | |
| 2004/0182831 A1 | 9/2004 | Cheng et al. | |
| 2008/0151259 A1 * | 6/2008 | Yoo | 356/521 |
| 2008/0238435 A1 | 10/2008 | Bockelman et al. | |
| 2008/0257023 A1 * | 10/2008 | Jordil et al. | 73/105 |
| 2009/0024241 A1 | 1/2009 | Rice et al. | |
| 2011/0240888 A1 * | 10/2011 | Rosenzweig et al. | 250/492.3 |
| 2012/0263347 A1 * | 10/2012 | Ichimaru | 382/103 |
| 2013/0190922 A1 * | 7/2013 | Chugg et al. | 700/186 |

FOREIGN PATENT DOCUMENTS

| | | |
|---|---|---|
| GB | 2 044 919 A | 10/1980 |
| WO | WO 01/69205 A1 | 9/2001 |
| WO | WO 2004/079405 A2 | 9/2004 |

OTHER PUBLICATIONS

International Search Report dated Oct. 27, 2011 issued in PCT/EP2011/067509.
European Search Report dated Sep. 29, 2011 issued in EP 11 27 5045.
UK Search Report dated Mar. 29, 2011 issued in GB1017412.6.

* cited by examiner

WORKPIECE POSITIONING METHOD AND APPARATUS

This invention relates to a method and apparatus for relatively positioning a workpiece and a reference axis. It is particularly but not exclusively applicable to the accurate presentation of an integrated circuit (microchip) to a pulsed laser, for example for performing single event effect (SEE) sensitivity mapping.

Conventional stepper-motor positioning for laser SEE scanning imposes restrictions on the trajectory and reproducibility of the scanning paths. In particular the scanning pattern generates unwanted accelerations and decelerations, which tend to induce vibrations in the structure in which the microchip is mounted.

The present invention, at least is its preferred embodiments, seeks to overcome or at least reduce this problem, but is of general application to the accurate relative positioning of a workpiece and an operative element required to interact with it. The operative element may be one which performs an operation on the workpiece, or tests or inspects it, or is assembled with it.

In one aspect the invention provides a method of relatively positioning a workpiece and a reference axis comprising effecting relative displacements of the workpiece and the reference axis along orthogonal axes so that an intersection of the reference axis with the workpiece is moved at substantially constant speed along a curvilinear path.

The displacements along the axes preferably are effectively continuous.

The curvilinear path may be a spiral.

Preferably the change in radius per revolution between successive turns of the spiral is constant. This results in the trajectory length per area in the x-y plane being constant, thereby facilitating uniform scanning coverage. Constant change in radius can be achieved when the displacements along the orthogonal axes are defined by $x=A\sqrt{t}\cos(\omega\sqrt{t})$ and $y=A\sqrt{t}\sin(\omega\sqrt{t})$ where t is time and A and $\omega$ are constants.

The origin of the spiral may be positioned relative to the workpiece whereby to reduce radial acceleration of the intersection. Thus, parts of the spiral closest to its origin may be omitted from the curvilinear path so as to make the peak acceleration (which occurs at the lowest performed radius from the origin, if the speed of execution is constant) arbitrarily low.

As noted above, the invention is particularly applicable to laser SEE sensitivity mapping. Thus the reference axis may be the propagation axis of a laser or other directed energy beam.

The laser may be a pulsed laser of constant pulse repetition frequency.

Preferably the spacing along the spiral of successive points in or on the workpiece illuminated by the laser pulses and the radial spacing of successive turns of the spiral about its origin are such as to produce an array of such points which is evenly distributed at constant density per unit scanned area of the workpiece. This can be achieved by making the spacing of said points along the spiral equal to the radial spacing of successive turns of the spiral about its origin.

Particularly but not exclusively for laser SEE sensitivity mapping, the invention provides a method of investigating an integrated circuit (IC) comprising disposing the IC as the workpiece in the method set forth above, exposing the IC to the laser pulses, and determining the effect on the IC of said pulses.

The method may comprise investigating the disposition of memory cells or other elements of the IC by exposing a said element at a point in or on the IC to a laser pulse so as to change the state thereof, and identifying the element from the change of state. Thus it is possible to associate a logical memory address with a physical location on the IC.

A preferred method comprises investigating the IC by exposing selected said points to laser pulses during at least two traverses of the curvilinear path, the laser power level being constant during each traverse, the power level during the second and subsequent traverses being different to (and preferably greater than) that during a previous traverse.

In another aspect the invention provides apparatus for relatively positioning a workpiece and a reference axis comprising x-wise displacement means and y-wise displacement means for effecting relative displacements of the workpiece and the reference axis along orthogonal axes, and control means configured to operate the displacement means, so that in operation an intersection of the reference axis with the workpiece is moved at constant speed along a curvilinear path.

The displacement means may comprise a piezoelectric transducer.

There may be a strain gauge sensor or other displacement sensing means arranged to provide feedback of the movement of said intersection to the control means.

In a further aspect the invention provides a computer readable medium having recorded thereon a computer program which when installed and operated performs the method set forth above.

An embodiment of the invention will now be described merely by way of example with reference to the accompanying drawings, where:

FIG. 3 shows a scanning pattern according to the invention; and.

Figure 1:
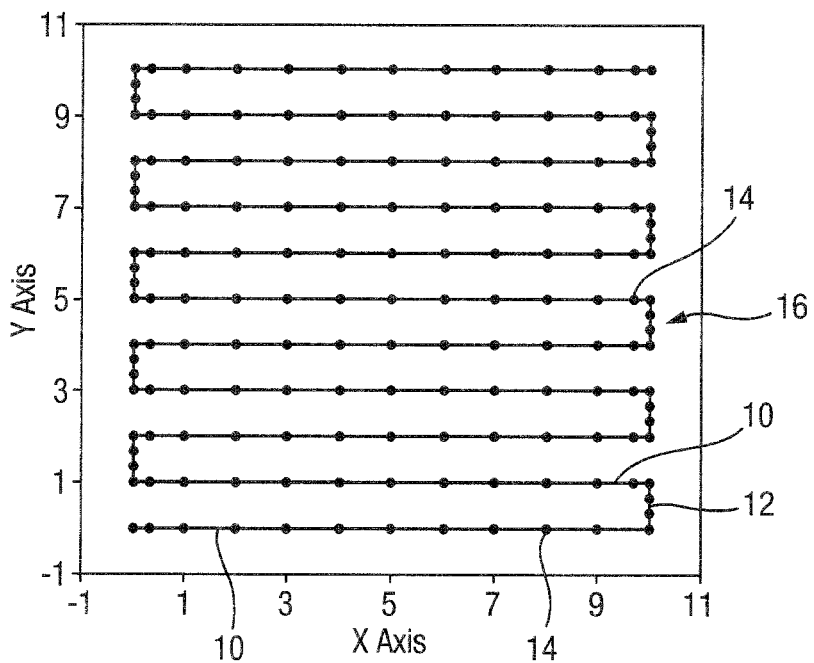
FIG. 1 shows a conventional scanning pattern used in laser SEE sensitivity scanning of a microchip.

This embodiment of the invention employs a combination of piezo-electric x-y positioning with a curvilinear scanning pattern to achieve the delivery of evenly-distributed arrays of laser pulses to a target area such as a microchip, the laser pulse repetition rate being constant. The embodiment simultaneously seeks to minimize accelerations of the positioning system, so as to minimize induced vibrations in the mount in order to be able to reproduce exactly super-imposable arrays of laser pulses at different laser pulse energies. The overall objective is rapidly to produce maps of laser pulse energy thresholds for upsets/failures induced in the target (e.g. memory bits in the IC flipped from a 1 to a 0 or vice versa).

Digital electronic equipment in satellites and high-flying aircraft is vulnerable to ionising particle radiation. The impact of a high energy particle on a cell of an integrated circuit can produce a temporary or permanent change in that cell, termed a single event effect (SEE) or single event upset (SEU). The mapping of SEE sensitivity at the cell level in memory devices and other integrated circuits can provide important insights into the vulnerability of the device to such effects. The derangement of a single cell by a SEE will introduce a single bit error. This generally can be overcome by error correction techniques, but compensating for the corruption of two bits in the same word is more difficult. This may occur as a result of a single irradiation event, if, for example, the memory cells storing bits from the same word are physically adjacent on the microchip die. Thus it is useful to know the physical location of each memory cell in the device, as well as its address, so that the cells can be utilised in a manner such that the bits of the same word are not stored in cells which are relatively near to each other or so that the appropriate level of error correction may be implemented in software, if it is impossible to avoid such adjacency. Alternatively, the results obtained with this invention can facilitate a decision to discard one microchip design in favour of a more SEE-tolerant design with an equivalent function from a different supplier.

SEE sensitivity mapping is undertaken by using laser pulses to simulate the incident ionising radiation events at a multiplicity of points on the microchip. Conventionally, the SEE thresholds are established by varying the laser pulse energy on a point by point basis. This is very time consuming.

In this described embodiment of the invention, an array of points on the microchip are instead exposed to a rapidly-delivered scan of laser pulses at a fixed energy level. The scan of the same points is then repeated at a somewhat higher fixed energy level and then again at successively further increased energy levels, as necessary. Each time the cells at some of the points suffer a SEU i.e. they change state, and their identity can be established by interrogating the chip after each laser pulse.

The technique is dependent for its success on the laser pulses being applied sufficiently accurately each time to the same points of the microchip. The stepper-motor positioning systems conventionally employed in SEE mapping cannot achieve this, and so we have devised an alternative solution.

Stepper motor positioning systems are constrained by a finite step size and cumulative positioning errors. Each move has distinct phases of acceleration followed by fixed velocity followed by deceleration. In general a raster scanning pattern such as shown in FIG. 1 is used. This consists of extended parallel rows 10 in one direction (here along the x-axis) with a short orthogonal step 12 at the end of the row to index the raster in the y-direction. Points on the microchip illuminated by a laser pulsing at a constant rate are shown at 14. Because of the sharp decelerations and accelerations at the ends of each x-wise row, and the relatively/low speed of traverse in the y direction, the points exposed to the laser pulses are densely clustered at the end of each row as at 16.

The accelerations and decelerations tend to induce vibrations in the mount on which the microchip is positioned, which limits the accuracy with which each laser spot can be positioned.

Figure 2:
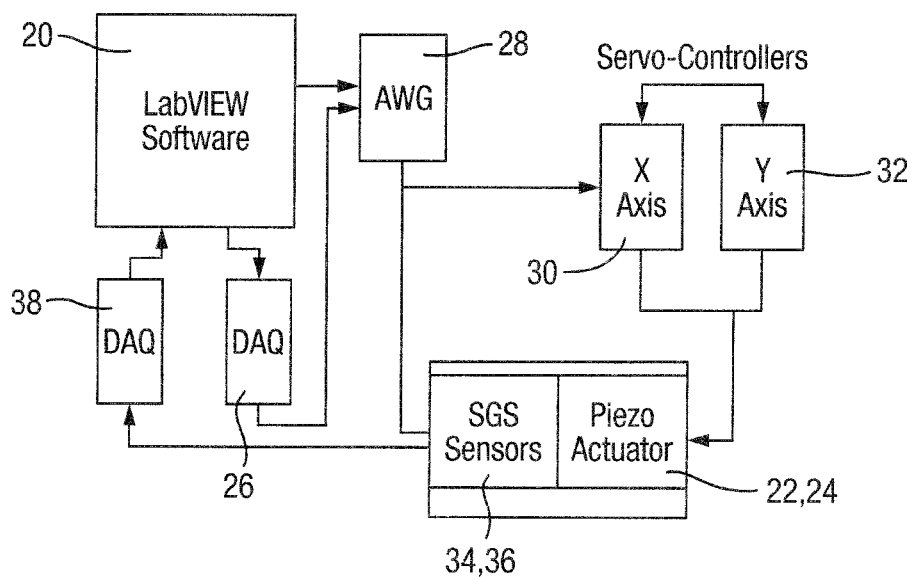
FIG. 2 shows apparatus according to the invention.

FIG. 2 shows an apparatus according to the invention. A microchip (not shown) is mounted on a platform which is approximately positioned relative to a pulsed laser source (not shown) by x and y stepper motors (not shown) as know per se. The platform is further accurately positionable relative to the stepper motors by x and y piezo actuators 22, 24. Those actuators are of the type known per se in positioning a target for scanning electron microscopy.

The system is controlled by a computer 20 running LabVIEW® or another virtual instrumentation program. The computer instructs a waveform generator 28 via a digital to analog converter 26 to produce respective waveforms for driving the x-axis and y-axis axis piezo-electric actuators 22, 24 via servo controllers 30, 32. The outputs of the servo controllers are continuous DC (analog) voltages, which are proportional to the displacements required of the piezo-electric actuators. Strain gauge sensors 34, 36 provide feedback of the platform position to the computer 20 via analog-to-digital converter 38.

Because the x and y displacements produced by the piezoelectric actuators 22, 34 are continuous and proportional to their driving voltages, curvilinear motion of the platform and hence the microchip may be produced by causing the computer 20 to supply appropriate waveform instructions to the waveform generate 20.

In order to achieve the requisite positioning accuracy and repeatability, it is desirable to minimise the vibrations induced in the positioning system assembly incorporating the microchip mounting platform. Since the natural resonant frequencies for this assembly are expected to be much greater (of order kHz) than the scanning frequencies (<100 Hz) used in delivering pulse arrays, the peak vibration/reverberation energy may be anticipated to be induced during the peaks of acceleration (positive or negative) of this assembly (i.e. there is no direct excitation of the resonances). Therefore we have devised a curvilinear scanning pattern which gives low magnitudes for the accelerations in the form of a spiral trajectory. In fact the peak acceleration can be made arbitrarily low by starting the scanning pattern at larger radius from the centre of the spiral, since the acceleration decreases as the radius of curvature increases. In such a case, the origin of the spiral may be offset from the microchip so as to be located some distance beyond its edge, with the result that only part of each turn of the spiral passes over the surface of the chip. The laser source can be gated so that it only produces pulses when it is passing over the chip.

Further parameters which define the exact form of the trajectory are:
1. The speed of travel of the laser spot, which is normally constant (i.e. such that the intersection of the laser pulse locations is evenly spaced along the path).
2. The radial separation between each revolution of the spiral about its origin is set equal to the spacing of laser pulses along the trajectory to achieve an overall even spread of pulse locations.

The equations for the x and y components of this trajectory may therefore be defined in terms of the time parameter t as follows:

$$x = A\sqrt{t}\, \text{Cos}(\omega\sqrt{t}) \text{ and } y = A\sqrt{t}\, \sin(\omega\sqrt{t})$$

These give a constant trajectory speed around the spiral, where A and ω are fitting parameters to scale the spiral array appropriately in a given application. Since the speed v is the product of the radius $A\sqrt{t}$ with the rate of change (derivative with respect to time) of the angle $\omega\sqrt{t}$, we can write:

$$v = \frac{A\omega}{2}$$

The change in radius per revolution is that Δr such that:

$$\Delta r = 2\pi A/\omega$$

Given that the distance between pulses along the trajectory should be similar to Δr in order to given an even spread of pulses, the time $\Delta t_p$ between pulses is given by:

$$v\Delta t_p = \Delta r = \frac{2\pi A}{\omega}$$

On substituting for v, $$\Delta t_p = \frac{4\pi}{\omega^2}$$

Hence ω is defined by the laser pulsing rate. To define A in terms of the maximum radius of the array $R_{max}$, we can use $$R_{max}^2 = x_{max}^2 + y_{max}^2$$

Hence:

$$t_{max} = (R_{max}/A)^2$$

Figure 3:
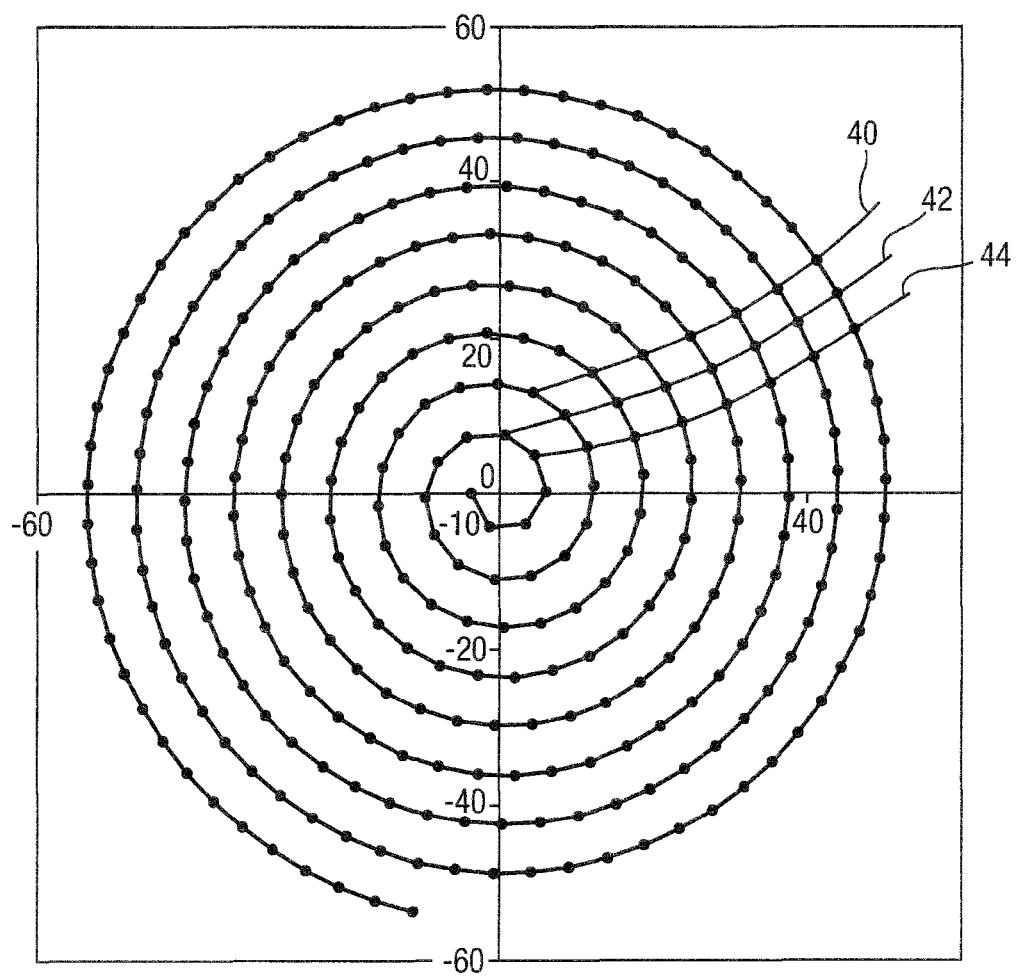

For the example array shown in FIG. 3, A=1 and ω=1 with $t_{max}$=3000 s and $\Delta t_p$=10 s.

It can be seen that the laser spots tend to lie in a repeating pattern of outwardly-extending curved lines, e.g. as at 40, 42, 44. It is necessary to read the monitored set of memory bits on the chip at least once in the period between successive laser pulses. Since the laser pulse repetition rate is about 100 Hz, there is insufficient time to read all the memory bits of a substantial (e.g. of order Mbits) memory. However we can reduce this task by perhaps a thousand fold by fixing a subset of the address lines at pre-set values and treating the memory as a smaller sized memory corresponding to the size of the remaining set of address lines. If this were done at random, then the read bits would usually be finely interspersed with a much larger set of unread bits, which would be ineffectual. However, if we have a large scale memory map available for the memory under test (which can itself be generated by laser pulsing the memory IC at a suitable set of locations and examining the addresses of the bits upset at each location), then we can identify the address lines that are known to control large scale positioning on the microchip die and by judiciously choosing the pattern of high and low states to which we pre-set these addresses, we can select small (normally rectangular) patches of adjoining bits. Within these patches the variable address lines are used to create read-cycles addressing the bytes of bits within the patch only. Due to the absence of external address lines to point at individual bits within bytes, it is normally inevitable that some bits of the same bytes will fall outside the patch being read, but this is not a serious constraint upon the general approach. Usually it is possible to read all (or at least a high proportion) of the bits within such a patch.

Figure 4:
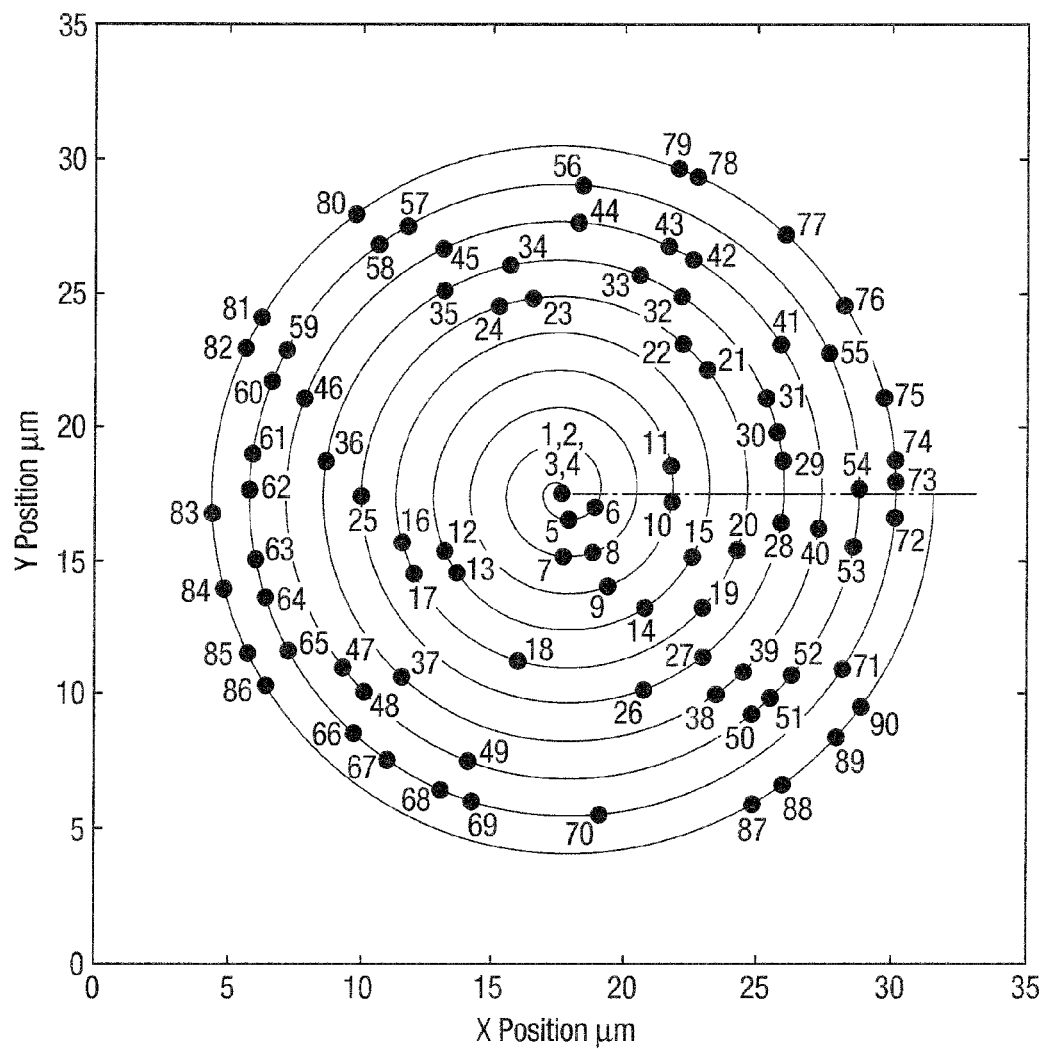
FIG. 4 illustrates points on an IC scanned using the invention.

FIG. 4 shows experimentally-observed single event upset (SEU) locations for a delivered spiral array of laser pulses plotted on the scanning path with the corresponding addresses and data being listed in table 1 below. The correct data at each address was hexadecimal 5A, so either bit 4 was flipped to 0 or bit 5 was flipped to 1 by the laser pulses, (i.e. 5A hexadecimal is 01011010 binary, 7A is 01111010 [fifth bit flipped from 0 to 1] and 4A is 01001010 [fourth bit flipped from 1 to 0]). The pulsed sub-region of the memory was read at a frequency of 40 Hz with a laser pulsing rate of 10 Hz; hence errors could be attributed to individual laser pulses. We have delivered such spiral arrays at a range of laser pulse energies, such that it is possible to derive upset threshold pulse energies across the investigated region of the device.

It can be seen that in this example (and as is generally the case) that the sensitivity to SEUs tends to be non-uniform across the microchip die. Knowledge of such patterns of sensitivity enables steps to be taken to reduce the possibility of bits of the same word being stored at locations which may suffer a SEU from the same ionising radiation event.

The invention includes any novel feature or combination of features herein disclosed, whether or not specifically claimed. The abstract as filed is repeated here as part of the specification.

A method of relatively positioning a workpiece and a reference axis comprising effecting relative displacements of the workpiece and the reference axis along orthogonal axes so that an intersection of the reference axis with the workpiece is moved at substantially constant speed along a curvilinear path. The method is particularly applicable to SEE sensitivity mapping of a microchip memory using a pulsed laser, relative to the axis of which the chip is moved in a spiral path.

TABLE I

ERROR ADDRESSES FOR THE LASER PULSING SPIRAL

| No | Address | Error | No | Address | Error | No | Address | Error |
|---|---|---|---|---|---|---|---|---|
| 1 | 00C799 | 7A | 31 | 00C159 | 7A | 61 | 00DE99 | 7A |
| 2 | 00C399 | 7A | 32 | 00CD59 | 7A | 62 | 00DC99 | 7A |
| 3 | 00C399 | 7A | 33 | 00D159 | 7A | 63 | 00D719 | 7A |
| 4 | 00C059 | 7A | 34 | 00DA59 | 7A | 64 | 00D719 | 7A |
| 5 | 00CB99 | 7A | 35 | 00D859 | 7A | 65 | 00D319 | 7A |
| 6 | 00C999 | 7A | 36 | 00D699 | 7A | 66 | 00C919 | 7A |
| 7 | 00C059 | 7A | 37 | 00C319 | 7A | 67 | 00C119 | 7A |
| 8 | 00C459 | 7A | 38 | 00ED99 | 4A | 68 | 00FD19 | 4A |
| 9 | 00FC59 | 4A | 39 | 00EF99 | 4A | 69 | 00F919 | 4A |
| 10 | 00C659 | 7A | 40 | 00F259 | 4A | 70 | 00F319 | 4A |
| 11 | 00CA59 | 7A | 41 | 00C359 | 7A | 71 | 00E799 | 7A |
| 12 | 00C299 | 7A | 42 | 00CB59 | 7A | 72 | 00EA59 | 4A |
| 13 | 00FE99 | 4A | 43 | 00CF59 | 7A | 73 | 00EE59 | 7A |
| 14 | 00F859 | 4A | 44 | 00D559 | 7A | 74 | 00ED59 | 7A |
| 15 | 00FE59 | 4A | 45 | 00DE59 | 7A | 75 | 00F359 | 4A |
| 16 | 00C499 | 7A | 46 | 00DD99 | 7A | 76 | 00FCD9 | 4A |
| 17 | 00C099 | 7A | 47 | 00CB19 | 7A | 77 | 00C0D9 | 7A |
| 18 | 00FA99 | 4A | 48 | 00C519 | 7A | 78 | 00C8D9 | 7A |
| 19 | 00F459 | 4A | 49 | 00FB19 | 4A | 79 | 00CCD9 | 7A |
| 20 | 00FA59 | 4A | 50 | 00ED99 | 4A | 80 | 00E259 | 7A |
| 21 | 00C559 | 7A | 51 | 00E999 | 4A | 81 | 00E799 | 7A |
| 22 | 00C959 | 7A | 52 | 00EB99 | 4A | 82 | 00E599 | 7A |
| 23 | 00D459 | 7A | 53 | 00EE59 | 4A | 83 | 00E099 | 7A |
| 24 | 00D459 | 7A | 54 | 00F259 | 4A | 84 | 00DB19 | 7A |
| 25 | 00CC99 | 7A | 55 | 00FB59 | 4A | 85 | 00D519 | 7A |
| 26 | 00F199 | 4A | 56 | 00D759 | 7A | 86 | 00D119 | 7A |
| 27 | 00F399 | 4A | 57 | 00E259 | 7A | 87 | 00E899 | 4A |
| 28 | 00F659 | 4A | 58 | 00E059 | 7A | 88 | 00E499 | 4A |
| 29 | 00FD59 | 4A | 59 | 00E399 | 7A | 89 | 00E599 | 4A |
| 30 | 00FD59 | 4A | 60 | 00E199 | 7A | 90 | 00E199 | 4A |

The invention claimed is:

1. A method of relatively positioning an integrated circuit (IC) and a propagation axis of a laser or other directed-energy beam comprising effecting relative displacements of the IC and the propagation axis along orthogonal axes so that an intersection of the propagation axis with the IC is moved at substantially constant speed along a curvilinear path.

2. The method of claim 1 wherein the displacements along the orthogonal axes are effectively continuous.

3. The method of claim 1 wherein the curvilinear path is a spiral.

4. The method of claim 3 wherein the change in radius per revolution between successive turns of the spiral is constant.

5. The method of claim 3, wherein the origin of the spiral is offset relative to the IC whereby to reduce radial acceleration of said intersection.

6. The method of claim 1 wherein the propagation axis is the propagation axis of a pulsed laser of constant pulse repetition frequency.

7. The method of claim 1 wherein the propagation axis is the propagation axis of a pulsed laser, the curvilinear path is a spiral and the spacing along the spiral of successive points in or on the IC illuminated by the laser pulses and the radial spacing of successive turns of the spiral about its origin are such that the distribution of the points over the scanned area of the IC is uniform.

8. A method of investigating an integrated circuit (IC) comprising the method of claim 1 wherein the propagation axis is the propagation axis of a pulsed laser, the method of investigating further comprising exposing the IC to the laser pulses, and determining the effect on the IC of said pulses.

9. The method of claim 8 comprising investigating the disposition of memory cells or other elements of the IC by exposing an element at a point in or on the IC to a laser pulse so as to change the state thereof, and identifying the element from the change of state.

10. The method of claim 9 comprising investigating the IC by exposing selected said points to laser pulses during at least two traverses of the curvilinear path, the laser power level being constant during each respective traverse, the power level of the second and subsequent traverses being different to the power level of a previous traverse.

11. A method for performing single event effect sensitivity mapping, comprising the method of claim 9, and further comprising fixing a subset of address lines for the elements of the IC at pre-set values prior to said exposure, thereby reducing the number of elements to be identified from the change of state.

12. A non-transitory computer readable medium having recorded thereon a computer program which when installed and operated causes a computer to perform the method of claim 1.

13. A method according to claim 1 wherein said relative displacements are effected by use of piezo actuators drivable by respective waveforms via servo controllers.

14. Apparatus for relatively positioning an integrated circuit (IC) and a propagation axis of a laser or other directed-enemy beam, the apparatus comprising x-wise displacement means and y-wise displacement means for effecting relative displacements of the IC and the propagation axis along orthogonal axes and control means configured to operate the displacement means so that in operation an intersection of the propagation axis with the IC is moved at constant speed along a curvilinear path.

15. The apparatus of claim 14 comprising a strain gauge sensor or other displacement sensing means arranged to provide feedback of the movement of said intersection to the control means.

16. Apparatus according to claim 14, wherein the displacement means comprises piezo actuators drivable by respective waveforms via servo controllers.

17. The apparatus of claim 14, wherein the apparatus is configured to operate the method of claim 1.

* * * * *